United States Patent [19]

Smith

[11] Patent Number: 5,849,800
[45] Date of Patent: Dec. 15, 1998

[54] USE OF AMANTADINE FOR TREATMENT OF HEPATITIS C

[75] Inventor: Jill P. Smith, Camp Hill, Pa.

[73] Assignee: The Penn State Research Foundation, University Park, Pa.

[21] Appl. No.: 826,249

[22] Filed: Mar. 28, 1997

[51] Int. Cl.⁶ .............................................. A61K 31/135
[52] U.S. Cl. ........................................................ 514/647
[58] Field of Search ............................................ 514/647

[56] References Cited

U.S. PATENT DOCUMENTS

| | | | |
|---|---|---|---|
| 3,310,469 | 3/1967 | Paulshock et al. | |
| 4,557,934 | 12/1985 | Cooper | 424/128 |
| 4,895,727 | 1/1990 | Allen | 424/642 |
| 5,427,909 | 6/1995 | Okamoto et al. | 435/54 |
| 5,428,145 | 6/1995 | Okamoto et al. | 536/23.72 |
| 5,436,126 | 7/1995 | Wang | 435/5 |
| 5,437,974 | 8/1995 | Ryan et al. | 435/5 |
| 5,502,080 | 3/1996 | Hitzig | 514/654 |
| 5,514,539 | 5/1996 | Bukh et al. | 435/5 |
| 5,527,669 | 6/1996 | Resnick et al. | 435/5 |
| 5,529,914 | 6/1996 | Hubbell et al. | 435/182 |
| 5,552,310 | 9/1996 | Yoshikura et al. | 435/235.1 |
| 5,573,934 | 11/1996 | Hubbell et al. | 435/177 |
| 5,574,132 | 11/1996 | Lacroix et al. | 530/323 |
| 5,580,718 | 12/1996 | Resnick et al. | 435/5 |
| 5,582,968 | 12/1996 | Wang et al. | 435/5 |
| 5,595,868 | 1/1997 | Habets et al. | 435/5 |
| 5,597,691 | 1/1997 | Houghton et al. | 435/23 |
| 5,599,998 | 2/1997 | Kraus | 564/455 |
| 5,601,844 | 2/1997 | Kagayama et al. | 424/489 |

OTHER PUBLICATIONS

Stevens et al., "Epidemiology of Hepatitis C Virus: A Preliminary Study in Volunteer Blood Donors," *JAMA* 263:49–53 (1990).
Choo et al., "Isolation of a cDNA Clone Derived from a Blood–Borne Non–A, Non–B Viral Hepatitis," *Science* 244:359–362 (1989).
Alter et al., "The Natural History of Community–Acquired Hepatitis C in the United States," *N. Engl J Med* 327(27):1899–1905 (1992).
Tong et al., "Clinical Outcomes After Transfusion–Associated Hepatitis C," *N Engl J Med* 332:1463–1466 (1995).
Liang et al., "Viral Pathogenesis of Hepatocellular Carcinoma in the United States," *Hepatology* 18:1326–1333 (1993).
Tsukuma et al., "Risk Factors For Hepatocellular Carcinoma Among Patients With Chronic Liver Disease," *N Engl J Med* 328:1797–1801 (1993).
Ascher et al., "Liver Transplantation For Hepatitis C Virus–Related Cirrhosis," *Hepatology* 20(suppl):24–27 (1994).
Davis et al., "Treatment of Chronic Hepatitis C With Recombinant Interferon ALFA A: A Multicenter Randomized, Controlled Trial," *N Engl J Med* 321(22):1501–1506 (1989).
Lunel et al., "Cryoglobulinemia in Chronic Liver Diseases: Role of Hepatitis C Virus and Liver Damage," *Gastroenterology* 106:1291–1300 (1994).

Misiani et al., "Interferon ALFA–2a Therapy In Cryglobulinemia Associated Hepatitis C Virus," *N Engl J Med* 330:751–756 (1994).
DeCastro et al., Hepatitis C Virus Antibodies and Liver Disease in Patients with Porphyria Cutanea Tarda, *Hepatology* 17:551–557 (1993).
Wilson et al., "Mooren's Corneal Ulcers and Hepatitis C Virus Infection," *N Engl J Med* 329:62 (letter) (1993).
Pawlotsky et al., "Immunological Disorders In C Virus Active Hepatitis; A Prospective Case–Control Study," *Hepatology* 19:841–848 (1994).
Di Bisceglie et al., "Recombinant Interferon Alfa Therapy For Chronic Hepatitis C," *N Engl J Med* 321:1506–1510 (1989).
Tiné et al., "Interferon For Non–A, Non–B Chronic Hepatitis: A Meta–Analysis of Radomised Clinical Trials," *J Hepatol* 13:192–199 (1991).
Taliani et al., "One Course Versus Two Courses of Recombinant Alpha Interferon In Chronic C Hepatitis," *Arch Virol Suppl* 4:294–298 (1992).
Marcellin et al., "Lack of Benefit of Escalating Dosage of Interferon Alfa In Patients With Chronic Hepatitis C," *Gastroenterology* 109:156–165 (1995).
Poynard et al., "A Comparison of Three Interferon Alfa–2b Regimens For The Long–Term Treatment of Chronic Non–A, Non–B Hepatitis," *N Engl J Med* 332:1457–1462, (1995).
Aoki and Sitar, "Clinical Pharmacokinetics of Amantadine Hydrochloride," *Clin Pharm* 14:35–51 (1988).
Skehel et al., "On The Mechanism of Inhibition of Influenza Virus Replication By Amantadine Hydrochloride," *J Gen Virol* 38:97–110 (1978).
Stokes et al., "Effects of Short–Term Corticosteroid Therapy In Patients With Chronic Non–A, Non–B Hepatitis (NANB)," *Gastroenterology* 92:1783 (abstract) (1993).
Di Bisceglie et al., "A Pilot Study of Ribavirin Therapy For Chronic Hepatitis C," *Hepatology* 16:649–654 (1992).
Hay and Zambon, "Multiple Actions of Amantadine Against Influenza Viruses," *Dev. Mol. Virol.* 4:301–315(1984).
Fiedler, *Lexicon Der Hilfastoffe Fur Pharmazie, Kosmetik Und Angrezende Gebiete* (Lexicon of Adjuvants for Pharmacy, Cosmetics an Related Areas) 191–195 (1971).
Urdea et al., "Branched DNA Amplification Multimers For The Sensitive, Direct Detection of Human Hepatitis Viruses," *Nucl Acids Sym* 24:197–200, (abstract) (1991).
Lau et al., "Significance of Serum Hepatitis C Virus RNA Levels In Chronic Hepatitis C," *Lancet* 341:1501–1509 (1993).
Adis Newsletters abstract of Higgins, "Symposia:Amantadine:effective alternative to interferon for hepatitis C?", Inpharma, 1028:15–16. May 1996.

*Primary Examiner*—Raymond Henley, III
*Attorney, Agent, or Firm*—Thomas J. Monahan

[57] ABSTRACT

Methods for treating patients with viral infection with pharmaceutical agents are disclosed. In one embodiment, the virus is Hepatitis C and the pharmaceutical agent is amantadine. The methods of the present invention can be used in patients that have not responded to or cannot tolerate interferon treatment, as well as patients under the age of eighteen.

21 Claims, 2 Drawing Sheets

USE OF AMANTADINE FOR TREATMENT OF HEPATITIS C

FIELD OF THE INVENTION

The present invention pertains to the treatment patients with viral disease utilizing pharmaceutical compositions. In particular, the present invention pertains to methods for the treatment of Hepatitis C viral infection in humans with amantadine.

BACKGROUND

Seropositivity to hepatitis C occurs in approximately 0.4–2% of the U.S. population and accounts for the overwhelming majority of cases of hepatitis [Stevens et al. JAMA 263:49–53, (1990)]. Recent knowledge of the gene structure of hepatitis C virus (HCV) has indicated that it is a single stranded RNA virus having a full length of about 9.5 kilobases [Choo et al. Science, Vol 244, pp. 359–362 (1989)]. Because HCV is a virus very likely to mutate and is not well understood how it replicates, the development of vaccines or anti-HCV drugs is still very slow.

Our understanding of the natural history of hepatitis C disease is evolving [Alter et al. N Engl J Med 327:1899–1905, (1992)]. Studies have shown that hepatitis C infection is associated with the development of advanced liver disease [Tong et al. N Engl J Med 332:1463–1466, (1995)] and hepatocellular carcinoma [Liang et al. Hepatology 18:1326–1333, (1993) and Tsukuma et al. N Engl J Med 328:1797–1801, (1993)], and liver failure due to hepatitis C infection is the most common indication for liver transplantation in many centers [Ascher et al. Hepatology 20 [suppl] :24–27, (1994)].

While many patients complain of fatigue [Davis et al. N Engl J Med 321:1501–1506, (1989)], a number of extrahepatic conditions have been associated with hepatitis C infection such as cryoglobulinemia [Lunel et al. Gastroenterology 106:1291–1300, (1994) and Misiani et al. N Engl J Med 330:751–756, (1994)], porphyria [DeCastro et al. Hepatology 17:551–557, (1993)], keratitis [Wilson et al. [letter]. N Engl J Med 329:62, (1993)] and autoimmune diseases [Pawlotsky et al. Hepatology 19:841–848, (1994)].

Currently, the only approved treatment for hepatitis C infection is α-interferon. Utilizing the standard therapy of 3 million units subcutaneously three times weekly for six months, approximately 50% respond with normalization of alanine aminotransferase (ALT) [Ascher et al. Hepatology 20 [suppl]:24–27, (1994)]. Unfortunately, half of those responding will relapse upon discontinuation of therapy [Davis et al. N Engl J Med 321:1501–1506, (1989) and Di Bisceglie et al. N Engl J Med 321:1506–1510, (1989)]. Most who are retreated will again relapse after drug withdrawal [Tiné et al. J Hepatol 13:192–199, (1991)].

In patients who do not respond to the initial interferon therapy, dose escalation has been attempted with little success [Taliani et al. Arch Virol Suppl 4:294–298, (1992) and Marcellin et al. Gastroenterology 109:156–165, (1995)]. Higher dose regimens result in an increased incidence of side effects including flu-like symptoms, depression, alopecia, and granulocytopenia [Davis et al. supra]. While longer duration of therapy with interferon is being advocated by some groups, complete response occurs in only one third of patients after eighteen months of therapy [Poynard et al. N Engl J Med 332:1457–1462, (1995)].

The low response rate with interferon as well as the high occurrence of side effects, has prompted investigators to search for other drugs which may be efficacious in the treatment of hepatitis C. What is needed is a new, effective treatment of Hepatitis C.

SUMMARY OF THE INVENTION

The present invention contemplates the treatment of patients with viral infection utilizing pharmaceutical agents. In one embodiment, the pharmaceutical agents of the present invention are cyclic amines and preferably cyclic primary amines. In one embodiment, the pharmaceutical agent is amantadine and the viral infection is Hepatitis C.

One embodiment of the present invention contemplates a) providing: i) a patient having symptoms of Hepatitis C infection, and ii) amantadine; and b) administration of a therapeutically effective dose of said amantadine to said patient under conditions such that said symptoms of said infection is reduced.

The present invention is not limited by the method of administration. In one embodiment, the administration is enteral administration. In another embodiment, said enteral administration is oral administration, and in another embodiment, said enteral administration utilizes polymeric microspheres.

On the other hand, in still another embodiment, said administration is parenteral administration. In these embodiments, said parenteral administration can be topical administration or by a transdermal patch. In another embodiment, said parenteral administration is subcutaneous administration. While in still another embodiment, said parenteral administration utilizes an aerosol.

The present invention is not limited by the nature of the patient. In one embodiment, said patient is a naive patient (e.g., has not undergone prior treatment for Hepatitis C infection), while in other embodiments said patient is untreatable with interferon (e.g., cannot tolerate interferon or whose condition is unresponsive to interferon). In still another embodiment, said patient is immunocompromised. In one embodiment, said patient is less than eighteen years of age.

The present invention is also not limited by the method of determining response to treatment. In one embodiment, said symptoms comprise elevated alanine aminotransferase levels in the blood (e.g., serum) of said patient, while in other embodiments, said symptoms comprise Hepatitis C ribonucleic acid or HCV antibody levels in said patient. In a yet another embodiment, said symptoms comprise the histology of a liver biopsy that is consistent with hepatitis C infection.

The present invention contemplates usage of many forms of amantadine. In one embodiment, said amantadine is in the form of a salt (e.g., amantadine hydrochloride).

Equally, the present invention is not limited by the type of Hepatitis C infection. In one embodiment, said Hepatitis C infection is chronic Hepatitis C infection, while in another embodiment, said Hepatitis C infection is acute Hepatitis C infection.

Definitions

As used herein, the term "enteral administration" means the introduction of a composition to a patient such that it is absorbed in the intestinal tract of the patient (e.g., pill, tablet, elixir, etc.)

As used herein, the term "oral administration" means the introduction of a composition to a patient through the oral cavity (i.e., in the mouth).

As used herein, the term "parenteral administration" means administration of a composition other than enteral (e.g., injection, transdermal, aerosol, etc.).

As used herein, the term "topical administration" means the introduction of a composition to a patient by application to the surface of the skin.

As used herein, the term, "subcutaneous administration" means introduction of a composition to a patient under the surface of the skin (e.g., injection with a hypodermic needle).

As used herein, the phrase "naive patient" refers to a patient that has not undergone prior treatment for Hepatitis C infection.

As used herein, the phrase "untreatable with interferon" refers to a patient that cannot tolerate the side-effects of interferon or whose viral infection is unresponsive to or has relapsed after interferon treatment.

As used herein, the phrase "immunocompromised" refers to a patient whose immune response is inhibited by medical condition such as leukopenia or autoimmune diseases (e.g., AIDS) or by intentional treatment (e.g., cyclosporin for organ transplant recipients).

As used herein, the phrase "chronic Hepatitis C infection" refers to an infection of a patient with the Hepatitis C virus that has lasted for more than six months.

As used herein, the phrase "acute Hepatitis C infection" refers to an infection of a patient by the Hepatitis C virus that has lasted for less than six months.

As used herein, the phrase "symptoms of Hepatitis C infection" refers to signs and evidence that are associated with Hepatitis C viral infection. Such signs and evidence may be subjective (e.g., fatigue) or objective (e.g., inflammation of the liver, elevated alanine aminotransferase levels in the blood, presence of HCV RNA or HCV antibodies).

DESCRIPTION OF THE INVENTION

Figure 1:
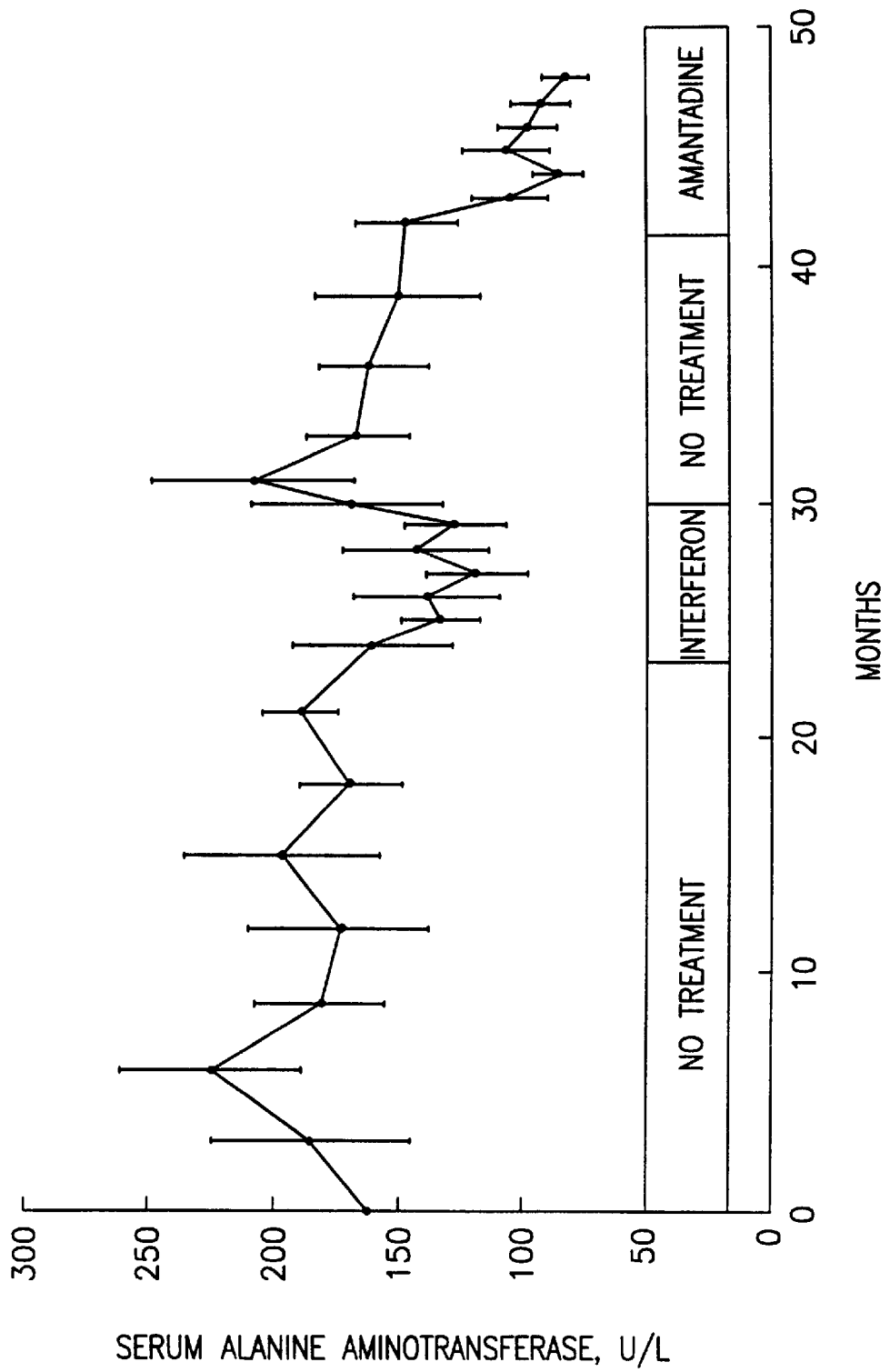
FIG. 1 illustrates the reduction of patient mean serum alanine aminotransferase following treatment with amantadine.

The present invention contemplates the use of a pharmaceutical agent for the treatment of viral infection. In one embodiment, the pharmaceutical agent is a cyclic amine and preferably a cyclic primary amine. In one embodiment, the pharmaceutical agent is amantadine.

Amantadine, a drug developed in the 1960s, has diverse uses ranging from prevention of influenza A infection to the treatment of Parkinson's disease [Aoki and Sitar, Clin Pharm 14:35–51, (1988)]. While an understanding of the precise mechanism is not necessary to carry out the methods of the present invention, it is believed that amantadine blocks events in late viral uncoating or early transcription [Skehel et al., J Gen Virol 38:97–110, (1978)]. Additionally, it is believed that the present invention induces release of dopamine from central dopaminergic neurons. Finally, it is believed that its ability to achieve high liver concentrations along with its antiviral properties may partially explain the reason why amantadine may be effective in patients with hepatitis C infection.

Numerous methods of identifying the presence of Hepatitis C in patients or biological samples have been developed. These include, but are not limited to the compositions of matter, devices and methods as set forth in U.S. Pat. Nos. 5,597,691; 5,580,718; 5,552,310; 5,527,669; 5,574,132; 5,514,539; 5,582,968; 5,437,974; 5,427,909; 5,428,145; 5,436,126 and 5,595,868, all herein incorporated by reference.

Treatment with amantadine offers several advantages over other treatment schemes (e.g., interferon). Unlike interferon, amantadine is readily absorbed when administered by the oral route, thus potentially improving patient safety and compliance. Amantadine is fairly well tolerated with few side effects, and the cost of amantadine is considerably less than interferon.

In addition to interferon, other agents such as corticosteroids [Stokes et al., Gastroenterology 92:1783 [abstract], (1993)] or ribavirin [Di Bisceglie et al., Hepatology 16:649–654, (1992)] have been shown to lower ALT levels in patients with HCV infection. However, this result is achieved without altering HCV RNA. This indicates that these treatments are useful against the inflammatory response in the liver to Hepatitis C infection, but do not treat the infection itself. On the other hand, the present invention decreased HCV RNA values in conjunction with diminution of ALT levels, demonstrating that the present invention not only decreases hepatic inflammation but also suppresses viral replication.

While the present invention is not limited by the nature of the prior treatment of the subject, it is contemplated that the present invention be utilized in patients who have not undergone prior treatment for their condition (i.e., naive patients), as well as patients who have not responded to interferon or other treatments. Thus, while retreatment or dose escalation with interferon in patients who have failed standard therapy has not been beneficial [Taliani et al., Arch Virol Suppl 4:294–298, (1992) and Marcellin et al., Gastroenterology 109:156–165, (1995)], in these patients, amantadine is useful.

Thus, the present invention is not limited by the sensitivities of the patient to other treatments, and in one embodiment it is contemplated that the present invention be used with patients who cannot tolerate the side effects of interferon. Additionally, since amantadine does not depress leukocyte counts or significantly augment immunity, in one embodiment the present invention is used in patients with leukopenia, autoimmune diseases, or organ transplants in addition to HCV. Unlike interferon, in one embodiment, the present invention is used in children under eighteen years of age with HCV.

1-Aminoadamantane hydrochloride (amantadine hydrochloride) is available commercially as an antiviral under the name Symmetrel (E. I. du Pont de Nemours and Company, Wilmington, Del.). Amantadine hydrochloride may also be prepared as known in the art, e.g., as described in U.S. Pat. No. 3,310,469. The present invention also contemplates the use of amantadine derivatives. For example, the (1-) position of adamantane has also been substituted with —CH(CH$_3$)NH$_2$ [U.S. Pat. No. 5,599,998 to Kraus, herein incorporated by reference]. The resulting compound is available commercially under the name Rimantadine which is also used in the treatment and prevention of influenza A.

While an understanding of the precise mechanism is not necessary to practice the methods of the present invention, it is believed that amantadine non-specifically inhibits viral entry into the cell by altering the pH of the endocytic vesicle. At lower concentration (about 5 microM), it is believed that amantadine exhibits a selective strain-specific inhibition of virus assembly [Hay and Zambon, Dev. Mol. Virol. 4:301–15(1984)].

The present invention is not limited by the method of administration of amantadine. In one embodiment, it is by conventional means available for use in conjunction with pharmaceuticals; either in combination with one another or in combination with other therapeutic agents. Other therapeutic agents include, but are not limited to, antiviral agents, such as interferon or ribavirin. It is contemplated that the methods of the present invention be administered alone or can be administered with a pharmaceutical carrier selected on the basis of the chosen route of administration and standard pharmaceutical practice.

In one preferred embodiment, amantadine is administered orally in solid dosage forms, such as capsules, tablets, or powders, or in liquid dosage forms, such as elixirs, syrups, and suspensions; however, it can also be administered parenterally, in sterile liquid dosage forms, or rectally in the form of suppositories.

One skilled in the art will be capable of adjusting the administered dose depending upon known factors such as the mode and route of administration; age, health, and weight of the recipient; nature and extent of symptoms, kind of concurrent treatment, frequency of treatment, and the effect desired. In one embodiment, the dosage is increased to overcome a non-responsive condition.

Additionally, amantadine can be employed in admixture with conventional excipients, i.e., pharmaceutically acceptable organic or inorganic carrier substances suitable for parenteral (e.g., topical application) or enteral (e.g., oral) which do not deleteriously react with the active compounds.

Suitable pharmaceutically acceptable carriers include but are not limited to water, salt solutions, alcohols, gum arabic, vegetable oils, benzyl alcohols, polyethylene glycols, gelatine, carbohydrates such as lactose, amylose, or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, merely to name a few. The pharmaceutical preparations can be sterilized and if desired mixed with auxiliary agents, e.g., lubricants, preservatives, stabilizers, wetting agents, emulsifier, salts for influencing osmotic pressure, buffers, coloring, flavoring, and/or aromatic substances and the like which do no deleteriously react with the active compounds. They can also be combined where desired with other agents, e.g. vitamins.

For enteral application, particularly suitable are tablets, liquids, drops, suppositories, or capsules. A syrup, elixir, or the like can be used wherein a sweetened vehicle is employed. Sustained or directed release compositions can be formulated, e.g., liposomes or those wherein the active compound is protected with differentially degradable coating, e.g., by microencapsulation, multiple coatings, etc.

In this manner, the present invention may be introduced into a subject in polymeric microspheres for the controlled release of the compound. Methods of producing microspheres from polymer can be found in U.S. Pat. No. 5,601,844 to Kagayama, et al. and U.S. Pat. Nos. 5,529,914 and 5,573,934 to Hubbel, et al., herein incorporated by reference.

For parenteral application, particularly suitable are injectable, sterile solutions, preferably oily or aqueous solutions, as well as suspensions, emulsions, or implants including suppositories. Nebulizers and inhalation aerosols may also be used. Ampules are in convenient unit dosages. It is also possible to freeze-dry the new compounds and use the lypophilizates obtained, for example, for the preparation of products for injection.

For other parenteral applications, such as topical applications and non-sprayable forms, viscous to semi-solid or solid forms comprising a carrier compatible with topical application and having a dynamic viscosity preferably greater than water. Suitable formulations include but are not limited to transdermal patches, solutions, suspensions, emulsions, creams, ointments, powders, liniments, salves, aerosols, etc., which are, if desired, sterilized or mixed with auxiliary agents, e.g., preservations, stabilizers, wetting agents, buffers, or salts for influencing osmotic pressure, etc.

Also suitable for topical application are sprayable aerosol preparations wherein amantadine, preferably in combination with a solid or liquid inert carrier material, is packaged in a squeeze bottle or in admixture with pressurized volatile, normally gaseous propellant, e.g., a freon. The application of these embodiments can be to the skin or mucous membrane or in the interior of the body and can be oral, peroral, enteral, pulmonary, rectal, nasal, vaginal, lingual, intervenous, intraarterial, intracardial, intramuscular, intraperitoneal, intracutaneous, subcutaneous. The parenteral preparations are preferably sterile or sterilized products.

In this manner, U.S. Pat. No. 4,895,727 to Allen, herein incorporated by reference, describes a method of inducing a reservoir effect in skin and mucous membranes so as to enhance penetration and retention and reduce transdermal flux of topically applied therapeutic and cosmetic pharmacologically active agents. U.S. Pat. No. 4,557,934 to Cooper, herein incorporated by reference, describes topical pharmaceutical compositions containing a pharmaceutically-active agent and the penetration enhancing agent, 1-dodecylazacycloheptan-2-one. This composition provides marked transepidermal and percutaneous delivery of the selected pharmaceutically-active agent.

Suppositories containing amantadine can be created using a suitable oleaginous or water-soluble base. The oleaginous class includes cocoa butter and fats with similar properties: the water-soluble class includes polyethylene glycols.

Other medicaments containing amantadine can be produced in a known manner, whereby the known and customary pharmaceutical adjuvants as well as other customary carrier and diluting agents can be used. Examples include, but are not limited to, gelatins, natural sugars such as sucrose or lactose, lecithin, pectin, starch (for example cornstarch), alginic acid, tylose, talc, lycopodium, silica (for example colloidal silica), glucose, cellulose, cellulose derivatives for example, cellulose ethers in which the cellulose hydroxyl group are partially etherified with lower aliphatic alcohols and/or lower saturated oxyalchohols, for example, methyl hydroxypropyl cellulose, methyl cellulose, cellulose phthalate, stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids ($C_{12}H_{24}O_2$ to $C_{18}H_{36}O_2$ and their mixtures), e.g. glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydricaliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g. glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane).

Other adjuvants can also be substances which bring about decomposition (so-called explosives) such as: cross-linked polyvinyl pyrrolidone, sodium carboxy methyl starch, sodium carboxy methyl cellulose or microcrystalline cellulose. Likewise, known coating agents such as e.g. polyacrylates, cellulose ethers and the like can be used.

For the production of solutions, there can be used water of physiologically compatible organic solvents, as for example, ethanol, 1,2-propylene glycol, polyglycols, e.g., diethylene glycol, triethylene glycol and dipropylene glycol and their derivatives dimethyl sulfoxide, fatty alcohols, e.g., stearyl alcohol, cetyl alcohol, lauryl alcohol and oleyl alcohol, triglycerides, e.g. glyceryl olelate glyceryl stearate, glyceryl palmitate, and glyceryl acetate, partial esters of glycerine, e.g., glyceryl monostearate, glyceryl distearate, glyceryl monopalmitate, paraffins, and the like.

For injectable solutions or suspensions, non-toxic parenterally compatible diluting agents or solvents can be used, for example: Water, 1,3 butane diol, ethanol, 1,2-propylene glycol, polyglycols in a mixture with water, Ringer's solution, isotonic solution of sodium chloride or also hardened oils including synthetic mono or diglycerides or fatty acids like oleic acid.

Known and customary solution assistants or emulsifiers can be used in the production of the preparations. The following are examples of solution assistants and emulsifiers which can be used: Polyvinylpyrrolidone, sorbitan fatty acid esters such as sorbian trioleate, phosphatides such as lecithin, acacia, tragacath, polyoxethylated sorbitan monooleate and other ethoxyated fatty acid esters of sorbitan, polyoxyethylated fats, polyoxyethylated oleotriglycerides, linolized oleotriglycerides, polyethylene oxide condensation products of fatty alcohols, alkyl phenolene or fatty acids or also 1-methyl-3-(2-hydroxyethyl) imidazolidone-(2). The term polyoxyethylated means in this context that the substances in question contain polyoxyethylene chains whose polymerization is generally between 2 to 40 and especially between 10 to 20.

Such polyoxyethylated substances can be obtained, for example, by reacting compounds containing hydroxyl groups (e.g. mono or diglycerides or unsaturated compounds such as, e.g., those containing the oleic acid residues) with ethylene oxide (e.g. 40 moles ethylene oxide per mole glyceride). Examples of oleotriglycerides are olive oil, peanut oil, castor oil, sesame oil, cotton seed oil and corn oil. [See also Fiedler, *Lexicon der Hilfastoffe fur Pharmazie, Kosmetik and angrezende Gebiete* [Lexicon of Adjuvants for Pharmacy, Cosmetics an Related Areas] pp. 191–195 (1971)].

Furthermore, there can be added preservatives stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred as neutral as possible to weak acid (to pH 5) pH value.

As antioxidants, there can be used, for example, sodium-meta bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride, and formalin derivatives.

The following example serves to illustrate certain preferred embodiments and aspects of the present invention and are not to be construed as limiting the scope thereof.

EXAMPLE: TREATMENT OF CHRONIC HEPATITIS C PATIENTS

This example establishes the safety and efficacy of amantadine in patients with chronic hepatitis C infection who had previously failed interferon therapy.

Diagnosis and Method

Twenty-two patients with chronic hepatitis C infection were enrolled in a study at the Milton S. Hershey Medical Center, Pennsylvania State University to evaluate the safety and efficacy of amantadine. HCV infection was documented by detection of anti-HCV and HCV RNA in serum. The diagnosis was confirmed by percutaneous liver biopsy in all except one patient who had a coagulation defect.

Patients were included who had not responded to therapy with interferon alfa-2b, having abnormal ALT values and detectable HCV RNA at the end of therapy. The previous dosage of interferon administered ranged from 3 to 10 million units (mean 4.6) three times weekly for 6 months in 15 patients and for 9 to 18 months in the remaining 7 patients. Laboratory values (aminotransferases, liver function tests, and complete blood count) were available and summarized from before (23.6±4.5 months), during, and after (12±2.6 months) interferon therapy.

Exclusion criteria included a prothrombin time greater than 2 seconds over control, a bilirubin greater than 2.0 mg/dl, encephalopathy, ascites, other forms of liver disease (i.e., autoimmune, hepatitis B, alcohol), pregnancy, psychiatric illness, severe medical conditions, or coinfection with HIV virus.

Patients were treated with amantadine-HCl 100 mg orally twice daily for six months. A physical examination, symptom survey, and laboratory tests were performed before and monthly while on the drug, and 6 months after stopping therapy. For analysis, patients were divided into one of three groups based upon responses in ALT and HCV RNA values: responders (normalization of ALT and loss of HCV RNA), partial responders (greater than 50% reduction in ALT and reduction in HCV RNA compared to the pre-treatment values), or non-responders (either no response or less than 50% reduction in ALT and HCV RNA values compared to pre-treatment levels). Patients were followed for an additional six months after the termination of amantadine to assess durability of response.

Laboratory Data

Monthly blood tests included serum ALT, aspartate aminotransferase, alkaline phosphatase, total bilirubin, complete blood count, and platelet count. Prothrombin time, serum iron, thyroid profile, and albumin were determined upon enrollment into the study and after termination of the drug. Levels of HCV RNA in serum were determined by the branched DNA signal amplification assay (Chiron, Emeryville, Calif.) [Urdea et al., Nucl Acids Sym 24:197–200, (1991)] prior to amantadine therapy and every 1–2 months while on therapy, as well as six months after discontinuation of drug. The sensitivity of this assay allows detection of HCV RNA at a level of $2\times10^5$ Eq/ml. If the HCV RNA values fell below this level of detectability, analysis was performed by RT-PCR [Laa et al., Lancet 341:1501–1509, (1993)] with a sensitivity capable of detecting 100 copies of HCV RNA. All serum samples were aliquoted in several smaller volumes and frozen at −70° C. to prevent degradation from thawing and refreezing should retesting be necessary.

Statistical Analysis

ALT values for each patient were recorded and averaged during each of the four time intervals. All the mean values in each time interval were then averaged for comparison so that equal weight was given to each patient. Statistical evaluation was performed utilizing analysis of variance and two-sample t-test, with significance determined at a level of $p<0.01$ to correct for multiple comparisons to control. Two patients who dropped out of the study due to side effects were considered treatment failures and were included in the non-responder group; data available from these patients was analyzed with the others by an intent-to treat basis.

Results

The characteristics of the patients upon enrollment into the study are shown in Table 1.

TABLE 1

Characteristics of the 22 Patients Upon Enrollment With Chronic Hepatitis C

| | |
|---|---|
| Age (years) | 43.4 ± 3.6 |
| Gender (% Males) | 16 (72%) |
| History of Blood Transfusion | 11 (50%) |
| Chronic hepatitis no. (%) | |
| Persistent hepatitis | 5 (23%) |
| Active Hepatitis | 12 (55%) |
| Cirrhosis | 4 (18%) |
| Alanine aminotransferase U/L | 193 ± 12.9 |

The age range of patients enrolling in the study was 17 to 74 years. The suspected source of hepatitis C was blood or blood product transfusions in 11, intravenous drug abuse in 7, and was unknown in 4 patients (Table 1).

Responders had lower HCV RNA levels compared to the non-responders. No differences in histology were noted between the groups, nor were there differences in mode of acquisition, although a larger number of non-responders had a history of blood transfusions.

Serum Alanine Aminotransferase and Virologic Responses

Twenty-two patients with chronic hepatitis C were started on amantadine at a dose of 200 mg daily in divided doses. Two patients developed intolerable side effects and drug was stopped at 3 and 5 weeks of treatment. The remaining 20 patients completed 6 months of therapy and have been followed for 6 to 18 months. The mean serum ALT values of the 22 patients which had been stable and not changed during the previous interferon therapy, or observation intervals, decreased by an average of 50% ($p=0.01$) during the six months of amantadine therapy. Furthermore, mean ALT values remained lower than pre-treatment levels 6 months following cessation of therapy.

FIG. 1 compares patient serum alanine aminotransferase levels with no treatment, during interferon therapy, no treatment following interferon therapy and during amantadine therapy. No statistically significant differences in ALT values occurred between the intervals without therapy or while on interferon. Treatment with amantadine, however, significantly lowered ALT levels compared to both intervals without therapy and compared to ALT values during interferon administration.

In 6 of the 22 patients (27%), serum ALT levels fell into the normal range during amantadine therapy. Serum levels of HCV RNA also decreased in these 6, falling into the undetectable range. In follow up, all 6 continued to have normal serum ALT levels and 4 remain HCV RNA negative by both RT-PCR and branched DNA assay. In 8 patients (36%), serum ALT levels fell by more than 50% but remained abnormal. Serum HCV RNA levels also decreased in these patients, but remained reactive. Eight patients (36%) failed to respond to amantadine (6 did not respond and 2 terminated early due to side effects). HCV RNA values decreased with amantadine from $27.5\pm7.7\times10^5$ Eq/ml to undetectable levels in the responder group and from $131\pm36$ to $69\pm30\times10^5$ Eq/ml in the partial responder group. Patients who responded to amantadine therapy had significantly lower pre-treatment HCV RNA titers than the non-responders ($p<0.01$).

Figure 2:
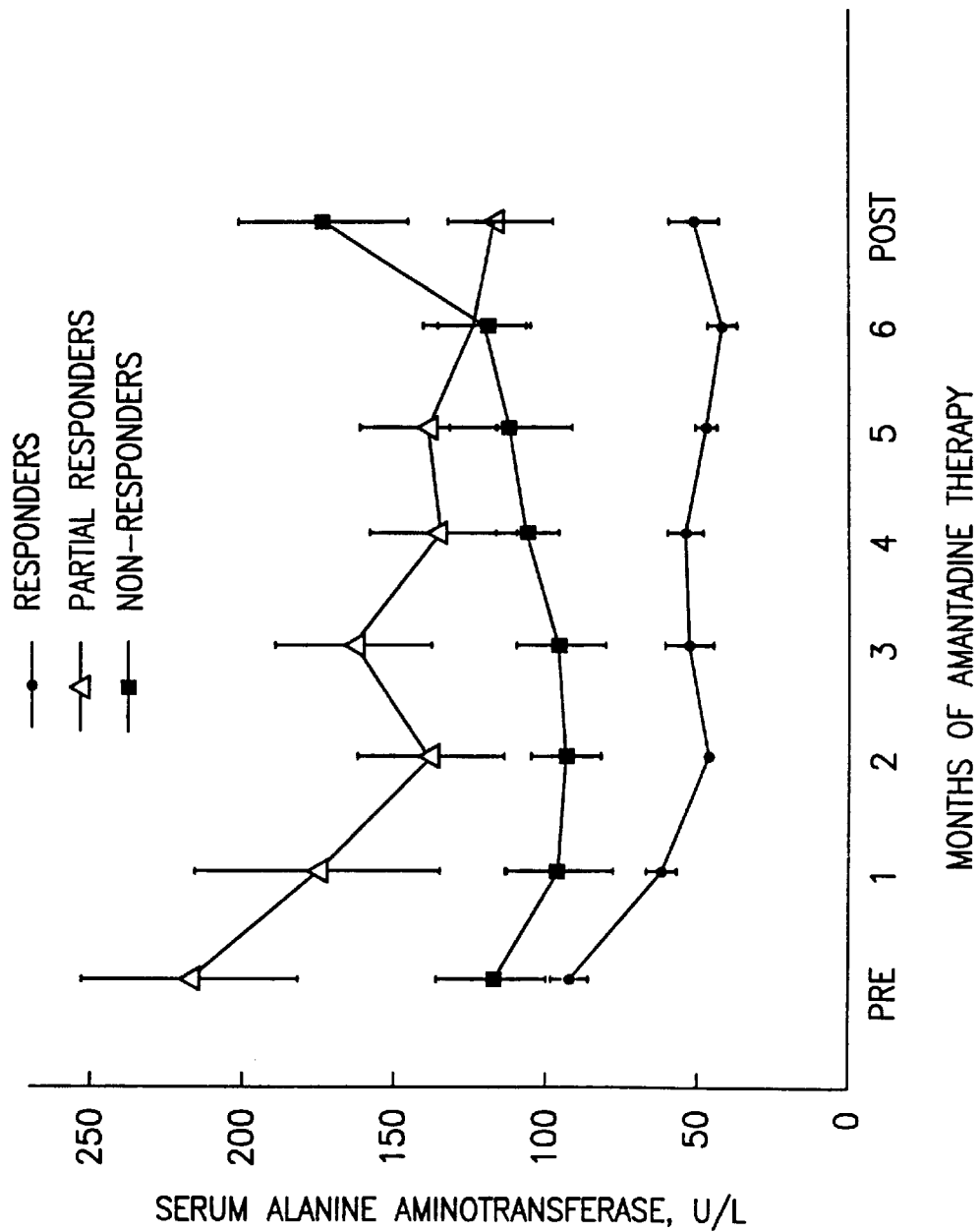
FIG. 2 illustrates the change in patient mean serum alanine aminotransferase levels over time with amantadine treatment.

FIG. 2 demonstrates the monthly patient serum alanine aminotransferase levels according to amantadine response. In responders, normalization of ALT occurred and partial responders achieved >50% reduction in ALT levels from baseline during the six month course of amantadine treatment. These ALT levels remained low after discontinuation of therapy.

Other Laboratory Values

There were no decreases in white blood count, hemoglobin, or platelet counts in patients treated with amantadine. Serum albumin levels improved slightly with therapy, but this difference was not significant. There were no changes in serum iron levels or thyroid tests during amantadine therapy.

Conclusion

The present study provides establishes antiviral activity with amantadine against hepatitis C virus. Among 22 patients who had not responded to an adequate course of interferon, 14 (64%) had marked improvements in serum ALT levels and decreases in HCV RNA titers during a six-month course of amantadine. No other single antiviral agent has thus far proven effective in patients who have failed to respond to interferon.

I claim:

1. A method of treating Hepatitis C infection in a human patient, consisting essentially of:
   a) providing:
      i) a patient having symptoms of Hepatitis C infection, and
      ii) a formulation consisting of amantadine; and
   b) administering a therapeutically effective dose of said formulation to said patient under conditions such that the symptoms of said infection is reduced.

2. A method of treating Hepatitis C infection in a human patient, comprising:
   a) providing:
      i) a patient having symptoms of Hepatitis C infection, and
      ii) a formulation comprising amantadine; and
      iii) a means for testing alanine aminotransferase levels in said patient;
   b) performing a first test with said means for testing to determine a first alanine aminotransferase level in said patient;

c) administering a therapeutically effective dose of said formulation to said patient; and d) performing a second test with said means for testing to determine a second alanine aminotransferase level in said patient, wherein said second level is lower than said first level.

3. The method of claim 1, wherein said administering is enteral administration.

4. The method of claim 3, wherein said enteral administration is oral administration.

5. The method of claim 4, wherein said enteral administration utilizes polymeric microspheres.

6. The method of claim 1, wherein said administering is parenteral administration.

7. The method of claim 6, wherein said parenteral administration is topical administration.

8. The method of claim 7, wherein said topical administration utilizes a transdermal patch.

9. The method of claim 6, wherein said parenteral administration is subcutaneous administration.

10. The method of claim 6, wherein said parenteral administration utilizes an aerosol.

11. The method of claim 1, wherein said symptoms comprise elevated alanine aminotransferase levels in said patient.

12. The method of claim 1, wherein said symptoms comprise Hepatitis C ribonucleic acid levels in said patient.

13. The method of claim 1, wherein said symptoms comprise Hepatitis C antibody levels in said patient.

14. The method of claim 1, wherein said amantadine is amantadine hydrochloride.

15. The method of claim 2, wherein said administering is enteral administration.

16. The method of claim 15, wherein said enteral administration is oral administration.

17. The method of claim 16, wherein said enteral administration utilizes polymeric microspheres.

18. The method of claim 2, wherein said administering is parenteral administration.

19. The method of claim 18, wherein said parenteral administration is topical administration.

20. The method of claim 19, wherein said topical administration utilizes a transdermal patch.

21. The method of claim 18, wherein said parenteral administration utilizes an aerosol.

* * * * *